United States Patent [19]

Schulz et al.

[11] 4,173,573

[45] Nov. 6, 1979

[54] PROCESS FOR PREPARING 3,4,3,4-BENZOPHENONE-TETRACARBOXYLIC DIANHYDRIDE

[75] Inventors: Johann G. D. Schulz, Pittsburgh; Anatoli Onopchenko, Monroeville, both of Pa.

[73] Assignee: Gulf Research and Development Company, Pittsburgh, Pa.

[21] Appl. No.: 921,571

[22] Filed: Jul. 3, 1978

[51] Int. Cl.$^2$ ............................................. C07D 307/89
[52] U.S. Cl. .................................................... 260/346.4
[58] Field of Search ...................................... 260/346.4

[56] References Cited

U.S. PATENT DOCUMENTS

| 3,002,034 | 9/1961 | Schulz et al. | 260/668 C |
| 3,078,279 | 2/1963 | McCracken et al. | 260/346.4 X |

*Primary Examiner*—Richard Raymond

[57] ABSTRACT

A process for preparing 3,4,3',4'-benzophenonetetracarboxylic dianhydride which comprises condensing an impure ortho-xylene mixture with acetaldehyde in contact with an acid catalyst to obtain an impure 1,1-bis(3,4-dimethylphenyl)ethane mixture, oxidizing the 1,1-bis(3,4-dimethylphenyl)ethane mixture with nitric acid to obtain a mixture of carboxylic acids, from which by crystallization and dehydration substantially pure 3,4,3',4'-benzophenonetetracarboxylic dianhydride is recovered.

9 Claims, No Drawings

PROCESS FOR PREPARING 3,4,3',4'-BENZOPHENONE-TETRACARBOXYLIC DIANHYDRIDE

BACKGROUND OF THE INVENTION

1. Field of the Invention

This invention relates to a novel process for preparing 3,4,3',4'-benzophenonetetracarboxylic dianhydride (BTDA) which comprises condensing an impure ortho-xylene mixture with acetaldehyde in contact with an acid catalyst to obtain an impure 1,1-bis(3,4-dimethylphenyl)ethane (DXE) mixture, oxidizing the DXE mixture with nitric acid to obtain a mixture of carboxylic acids from which by crystallization and dehydration substantially pure BTDA is recovered.

2. Description of the Prior Art ortho-Xylene, as well as other isomeric xylenes, are readily obtained from petroleum crudes through catalytic reforming or cracking as part of a $C_8$ aromatic stream. A typical $C_8$ aromatic distillate fraction from a refinery stream has the following composition:

TABLE I

| Compound | Boiling Point, °C. | Volume Per Cent Broad | Volume Per Cent General |
|---|---|---|---|
| Components Boiling Below Ethylbenzene[1] | <136 | 0 to 10 | 0 to 2 |
| Ethylbenzene | 136 | 12 to 30 | 15 to 25 |
| para-Xylene | 138 | 15 to 25 | 16 to 20 |
| meta-Xylene | 139 | 30 to 50 | 35 to 48 |
| ortho-Xylene | 144 | 12 to 30 | 12 to 28 |
| Components Boiling Above ortho-Xylene[2] | >144 | 0 to 10 | 0 to 5 |

[1]Mostly toluene
[2]Cumene, pseudocumene, mesitylene, etc.

By far the most important component commercially in the above distillate fraction is para-xylene, an important feedstock for the production of terephthalic acid. The second most important component, ortho-xylene, is a starting material for the production of phthalic anhydride via vapor phase oxidation.

Numerous literature references exist for the isolation of individual components present in the above mixture, for example, in U.S. Pat. Nos. 3,636,180 to D. B. Broughton, 3,653,184 to B. M. Drinkard et al, 3,707,550 to L. O. Stine, 3,715,409 to D. B. Broughton, 3,700,744 to V. Berger et al, etc.

In a typical procedure, for example a $C_8$ aromatic distillate fraction, as defined in Table I, is separated into relatively pure components using a combination of molecular sieve adsorption, fractionation and isomerization steps. In the first, para-xylene and ethylbenzene are sorbed, leaving a raffinate of ortho- and meta-xylene. The sorbed components are desorbed with diethylbenzene, which is recovered by fractionation and ethylbenzene is separated from para-xylene in a second adsorption step. The sorbed para-xylene is desorbed with toluene, which is recovered by fractionation. The raffinate from each of the adsorption steps contain desorbent, which is recovered by fractionation. The ortho- and meta-xylene mixture is isomerized to obtain additional para-xylene and the isomerizate is fractionated to remove light ends and to recover a crude ortho-xylene fraction. A typical crude ortho-xylene fraction so obtained will have the following composition:

TABLE II

| Compound | Volume Per Cent Broad | Volume Per Cent General |
|---|---|---|
| ortho-Xylene | 88 to 98 | 94 to 96 |
| meta-Xylene | 0 to 3 | 0 to 2 |
| para-Xylene | 0 to 2 | 0 to 1 |
| Ethylbenzene | 0 to 1 | 0 to 1 |
| Components Boiling Above ortho-Xylene | 0 to 3 | 0 to 2 |

The crude (or impure) ortho-xylene fraction so recovered requires no further purification for the synthesis of phthalic anhydride, since the other components present which are not converted to phthalic anhydride are degraded during the vapor phase oxidation to carbon dioxide and water. In the event an ortho-xylene fraction of higher purity is desired, for example, greater than 99 percent, typically 99.7 percent or better, the crude fraction is subjected to further distillation under more closely controlled and more efficient conditions involving additional expense. For over ten years, for reasons set forth below, ortho-xylene of such higher purity has been used commercially in operations leading to the production of 3,4,3',4'-benzophenonetetracarboxylic acid (BTA), an intermediate in the manufacture of BTDA.

It would appear to one skilled in the art that the most direct route for the preparation of BTDA would be through the oxidation of the corresponding bis(3,4-dimethylphenyl) methane (DXM I), since relatively inexpensive air or molecular oxygen could be used as the oxidant. See, for example, U.S. Pat. No. 3,652,598 to R. L. Broadhead. Furthermore, to convert the bridging methylene group ($CH_2$) in DXM to a carbonyl bridge even if nitric acid were used as oxidant, would theoretically require only about 1.33 mols of nitric acid per mol of DXM as seen from the following equation:

$$3\text{-CH}_2\text{--} + 4HNO_3 \longrightarrow 3 \overset{|}{\underset{|}{C}}=O + 4NO + 5H_2O. \tag{1}$$

To convert each methyl substituent on the DXM molecule to a carboxyl group would theoretically require two mols of nitric acid as seen from the following equation:

$$-CH_3 + 2HNO_3 \rightarrow -COOH + 2NO + 2H_2O. \tag{2}$$

Therefore to convert DXM to BTA using nitric acid as oxidant would theoretically require a total of 9.33 mols of nitric acid.

Unfortunately, in synthesizing DXM through the alkylation of ortho-xylene with formaldehyde only from about 78 to about 87 percent of DXM I, is obtained, with the remaining 13 to 27 percent being the isomers (3,4-dimethylphenyl-2,3-dimethylphenyl)methane (DXM II)

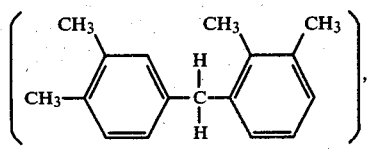

and bis(2,3-dimethylphenyl)methane (DXM III)

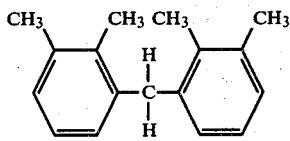

(See M. I. Farberov et al, Zhurnal Organicheskoi Khimii, Volume 4, No. 1, pages 163–178, 1968.)

The three isomers so obtained are next to impossible to separate from each other either at the hydrocarbon stage or after oxidation with nitric acid to acids. Therefore, after dehydration, an isomeric mixture of dianhydrides is obtained. We have found the dianhydride product so produced to be a low-melting solid, having a melting point around 150° C., with the various dianhydride isomers exhibiting varying degrees of reactivity, and the properties of polymers produced therefrom, particularly polyimides, to be unacceptable. Thus, M. I. Farberov et al clearly state that "... for preparation of polymers isomeric anhydrides must not be present in these as impurities..." Additional problems that can be present during dehydration of the above oxidized mixture is the formation of lactones between a bridging carbonyl group and the carboxyl group located in the ortho position with respect to this carbonyl function, a significant problem in U.S. Pat. No. 3,652,598 to R. L. Broadhead.

The commercial production of BTDA has involved the nitric acid oxidation of DXE I. This is because it has been found that in condensing ortho-xylene with acetaldehyde to produce DXE I, the protonated acetaldehyde, because of its larger size compared to the corresponding protonated formaldehyde, reacts more slowly, and therefore more selectively, to give from about 98 to 99 percent of the desired DXE I isomer,

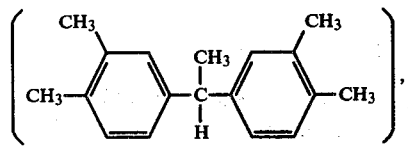

and only from about one to two percent of 1,1-(3,4-dimethylphenyl-2,3-dimethylphenyl)ethane (DXE II),

and 1,1-bis(2,3-dimethylphenyl)ethane (DXE III),

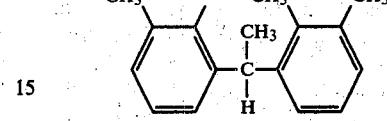

(See M. I. Farberov et al referred to above).

Commercial oxidation of the above DXE mixture with nitric acid, requiring theoretically 3.33 mols of nitric acid per ethylidene group oxidation, or a total

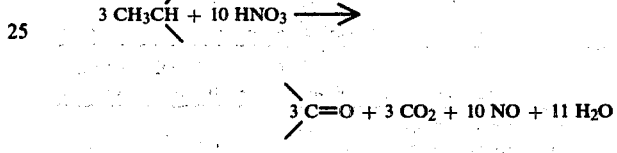

of 11.33 mols of nitric acid per mol of DXE, followed by dehydration of the resulting oxidation product, has led to substantially pure BTDA having a high melting point (226° C.), and uniform reactivity. This material has been used in the preparation of polymers, for example, polyamide, having excellent properties.

SUMMARY OF THE INVENTION

We have found, unexpectedly, that if an impure ortho-xylene mixture, such as defined in Table II, is used, instead of substantially pure ortho-xylene in the condensation reaction to obtain DXE, and if the latter product is then oxidized with nitric acid, a BTA product is obtained which after dehydration produces BTDA, in yields and purity unaffected.

This is most unusual. Analysis of a typical ortho-xylene stream falling within the range of the impure product defined in Table II is as follows:

TABLE III

| Compound | Volume Per Cent |
|---|---|
| Ethylbenzene | 0.17 |
| para-Xylene | 0.30 |
| meta-Xylene | 2.52 |
| ortho-Xylene | 95.00 |
| Components Boiling Above ortho-Xylene | 2.01[1] |

[1] Of which 0.91 is cumene.

In synthesizing DXE from the above stream, each of the above compounds would be expected to react as follows with the more-abundant ortho-xylene.

TABLE IV (I) ortho-Xylene + ortho-Xylene 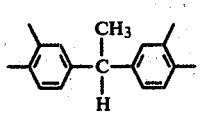 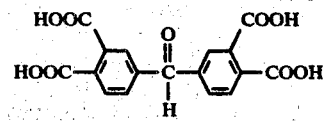

TABLE IV-continued

| | | |
|---|---|---|
| (II) ortho-Xylene + para-Xylene | 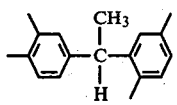 | 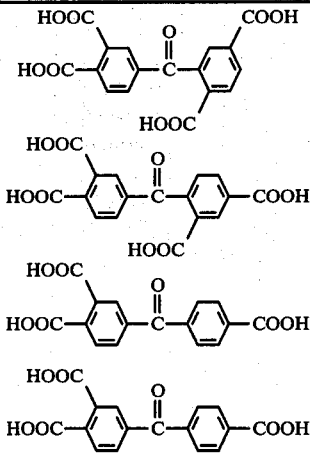 |
| (III) ortho-Xylene + meta-Xylene | 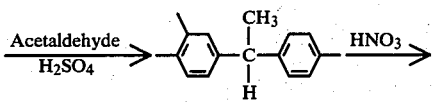 | |
| (IV) ortho-Xylene + Ethylbenzene | 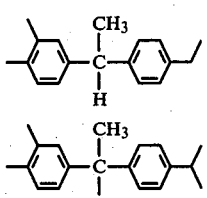 | |
| (V) ortho-Xylene + Cumene | | |

The above equations would lead one to believe that if the impure ortho-xylene contained five percent impurity, as above, twice as much, or 10 percent, of the product formed would not be converted to desired BTDA in the subsequent nitric acid oxidation and dehydration steps. Since we have found that Equation I is only about 98 to 99 percent efficient, the net loss of condensation product would be on the order of 11 to 12 percent. This would then make this reaction as inefficient as if the DXM mixture defined above, produced by the reaction of substantially pure ortho-xylene and formaldehyde, had been used in the process for producing BTDA. Additional problems envisioned in using impure ortho-xylene lie in the fact that many of the carboxyl groups produced in Equations II to V are either on non-adjacent positions, and therefore cannot form anhydrides, or are simply present as monocarboxylic acids. The presence of carboxyl groups in polyimides, for example, in more than trace amounts cannot be tolerated, since these acids act as transfer agents, preventing the build-up of viscosity and therefore result in low molecular weight polymers. Products, such as those obtained in Equations II and III, can additionally lead to lactones. However, as will be shown hereinafter, the use of an impure ortho-xylene mixture in the process leading to BTDA claimed herein results in yields and purity of BTDA as high as when substantially pure ortho-xylene is used.

The reaction conditions used in the condensation of ortho-xylene with acetaldehyde, the nitric acid oxidation of the condensation product and the dehydration of the reaction product to obtain the desired BTDA are those conventionally employed. A procedure that can be used to make the condensation product is disclosed, for example, in U.S. Pat. No. 3,002,034 to J. G. D. Schulz. Thus, in the condensation step, about two to about 20 moles, preferably about 2.5 to about five mols of the impure ortho-xylene mixture, as defined above in Table II, are mixed with a mol of acetaldehyde and the resulting mixture is gradually added to about 1.5 to about 10 mols of acid, preferably about 1.6 to about five mols of acid catalyst, while stirring, such as concentrated sulfuric acid per mol of aldehyde feed. Other useful catalysts include hydrofluoric acid, p-toluenesulfonic acid, etc. The resulting mixture is maintained at a temperature of about 5° to about 60° C., preferably about 10° to about 30° C., and a pressure of about 0 to about 200 pounds per square inch gauge (about atmospheric to about 13.6 kilograms per square centimeter), preferably about atmospheric pressure, for a period of about five minutes to about five hours, preferably about five minutes to about 60 minutes. At the end of the reaction period the aqueous phase is separated from the organic phase, for example, by decantation and the organic phase is neutralized, for example, using aqueous sodium hydroxide. The organic phase is then subjected to distillation to strip off unreacted ortho-xylene therefrom, followed by distillation of the desired DXE mixture used herein.

The nitric acid oxidation of a DXE mixture is also old and well known, as for example, in U.S. Pat. No. 3,078,279 to McCracken et al. The DXE product obtained above is subjected to oxidation with nitric acid having a concentration of about 5 to about 70 percent, preferably about 20 to about 40 percent. The amount of nitric acid employed, determined as the molar ratio of 100 percent nitric acid relative to the total components in the charge, is about 8.0 to about 17.0, preferably about 8.0 to about 12. The residence time required for the oxidation can be from about one minute to about 48 hours, preferably about 10 minutes to about two hours. Temperatures of about 110° to about 350° C., preferably about 150° to about 250° C., can be employed. Pressures sufficient to maintain the reaction system primarily in the liquid phase, from about atmospheric to about 500 pounds per square inch gauge or higher, are satisfactory. Upon completion of the reaction, the reaction product is permitted to cool down, preferably to room temperature, until a solid crystalline precipitate is formed. This may require, for example, from about 4 to about 24 hours. The crystals so obtained, substantially pure BTA, are separated from the liquid in any convenient method, for example, filtration.

The dehydration of BTA to BTDA is also known, as for example, in said U.S. Pat. No. 3,078,279. Thus, the BTA crystals can be dehydrated, for example, at a temperature of about 110° to about 320° C., preferably about 150° to about 280° C., in a vacuum oven for about one-half to about 24 hours, preferably about one to about 16 hours to obtain the substantially pure BTDA.

DESCRIPTION OF PREFERRED EMBODIMENTS

Example I

At atmospheric (ambient) pressure a mixture containing four mols of ortho-xylene and one mol of acetaldehyde was gradually added over a period of 30 minutes while stirring to a reactor containing three mols of concentrated sulfuric acid maintained at a temperature of 20° C. The ortho-xylene used reactant contained 99.9 volume percent ortho-xylene, trace amounts of meta- and para-xylene and 0.1 volume percent of $C_9$ aromatic components. The reaction was permitted to proceed for 15 minutes after addition was completed. The product was transferred to a separatory funnel and allowed to settle for one-half hour until phase separation occurred. The bottom aqueous layer containing sulfuric acid was withdrawn, and the organic product was then neutralized with 10 percent aqueous sodium hydroxide and distilled to remove unreacted ortho-xylene therefrom. The remaining fraction, having a boiling point range at atmospheric pressure of 328°–335° C., was substantially pure DXE (99+ percent).

To a one-gallon, 316-stainless steel, magnetically-stirred autoclave, equipped with cooling coils and a heating mantle there was added 354 grams of DXE and 284 grams of water. The autoclave was sealed, heated to 140° C., at which point 720 grams of 54 percent aqueous nitric acid was introduced over a period of three hours and then an additional 720 grams of 54 percent aqueous nitric acid over a period of one hour. The temperature was then raised to 175° C. and an additional 720 grams of 54 percent aqueous nitric acid was added over a period of one hour. The reaction was continued for an additional hour after the last addition of nitric acid. The pressure relief device was arbitrarily set to maintain a pressure below 1000 pounds per square inch gauge (68 kilograms per square centimeter) during the reaction. The autoclave was cooled to atmospheric (ambient) temperature, depressured to atmospheric pressure and the completely homogeneous solution (pale yellow in color) was withdrawn. A weighed one-half gram sample of the product solution was taken to dryness in a rotary evaporator and analyzed by gas liquid chromatography for the BTA content. From this data the analytical yield of the product was determined. The total filtrate was allowed to stand undisturbed for three hours, resulting in the crystallization of solids. Filtration, washing with a minimum amount of water and drying in a vacuum oven at 75° C. for six hours resulted in the recovery of 390 grams of BTA, corresponding to a yield of 73 percent.

Example II

Example I was repeated except that 354 grams of the impure ortho-xylene mixture defined in Table III was used in place of the substantially pure ortho-xylene of Example I.

Example III

Example II was repeated to verify the results obtained therein.

Example IV

Example II was repeated except that at the end of the third addition of nitric acid the reaction was continued for an additional two hours instead of one hour.

The results obtained in the above runs are summarized below in Table V.

Example V

Example II was repeated using 354 grams of aromatic feed containing 88 weight percent of DXE, (derived from 95 weight percent ortho-xylene) seven weight percent ortho-xylene and five weight percent of compounds boiling higher than DXE. The BTA isolated via crystallization amounted to 320 grams (76 percent yield). One-third of the total nitric acid was added at 140° C. over 3.7 hours and the remaining two-thirds at 175° C. over 1.75 hours. Reaction was stopped after holding for one hour under final conditions.

TABLE V

| Example | I | II | III | IV | Average of Examples II, III and IV | V |
|---|---|---|---|---|---|---|
| Theoretical Amount of 3,4,3',4'-BTA Expected, Grams | 532 | 479 | 479 | 479 | 479 | 421 |
| Actual Amount of 3,4,3',4'-BTA* Obtained, Grams (Per Cent Yield) | 390(73) | 356(74) | 352(73) | 366(75) | 358(74) | 320(76) |

*3,4,3',4'-benzophenonetetracarboxylic acid

The data in Table V show the unexpected results obtained operating in accordance with the process defined and claimed herein. In Example I wherein a substantially pure ortho-xylene was used the desired BTA, precursor for BTDA, was obtained in 73 percent yield. In each of Examples II, III and IV wherein an impure ortho-xylene mixture was used in an otherwise identical process, the yields were practically identical to the yield obtained in Example I.

In order to determine the purity of the BTA obtained above, the crystallized BTA obtained in each of Examples I and II was analyzed by gas liquid chromatography and the neutral equivalent was obtained. The data are summarized below in Table VI.

TABLE IV

| Run No. | I | II |
|---|---|---|
| Purity, Per Cent (Gas Liquid Chromatography) | 99.3[1] | 99.5[1] |
| Neutral Equivalent | 92.6[2] | 92.5[3] |

[1]Only impurity noted was trimellitic acid
[2]Average of two runs (92.1 amd 93.0)
[3]Average of two runs (91.8 amd 92.5)

Example V

In order to determine whether or not the BTDA produced herein would be just as acceptable commercially as BTDA prepared from analytical grade ortho-xylene, it was determined to carry out the highly-sensitive polyimide test. Accordingly, a sample of the BTA produced in Example II was melt dehydrated in a vacuum oven at 270° C. for one hour to obtain BTDA. A polyimide film was prepared from the resulting BTDA and tested as follows.

A solution of 10.0 g. (0.05 mol) of 4,4'-diaminophenylether in 115 cc. of water-free dimethylacetamide was prepared in a 250 cc. flask fitted with a stirrer, powder addition apparatus and a glass tube for sample removal for measurement of viscosity. The flask was closed to the atmosphere to exclude moisture. Over a two hour period 16.4 g. (0.0509 mol) of powdered BTDA was added with stirring. There was an exothermic reaction but the temperature was maintained below 40° C. by the controlled addition of the dianhydride to avoid conversion of polyamic acid to polyimide. The viscosity of the solution increased to Gardner K at the end of the reaction. The solution contained about 20 weight percent polyamic acid.

A film of this solution was cast on sheet Mylar (polyethylene terephthalate) using a Bird applicator set at 10 mils (0.25 mm.). The film was dried one-half hour at 150° C., in a circulating air oven. The resulting self-supporting film was stripped from the Mylar and was placed on a metal plate with metal strips holding the film in place. The final cure was completed step-wise from 200° to 300° C. by increasing the temperature over a period of about one hour with 300° C. maintained for one-half hour. The resulting film of about 1 mil (0.025 mm.) thickness was clear, yellow and transparent. The F.E.T. (folding endurance test), ASTM D-2176, on a series of strips cut from the film resulted in an average of over 15,000 folds for strips taken lengthwise to the direction of casting and an average of over 15,000 folds for samples taken transversely to the direction of casting.

Obviously, many modifications and variations of the invention, as hereinabove set forth, can be made without departing from the spirit and scope thereof and, therefore, only such limitations should be imposed as are indicated in the appended claims.

We claim:

1. A process for preparing 3,4,3',4'-benzophenone-tetracarboxylic dianhydride which comprises condensing an impure ortho-xylene mixture, said impure ortho-xylene mixture containing at least one of meta-xylene, para-xylene, ethylbenzene and cumene, with acetaldehyde in contact with an acid catalyst to obtain an impure 1,1-bis(3,4-dimethylphenyl) ethane mixture, oxidizing the mixture with nitric acid to obtain a mixture of carboxylic acids, from which by crystallization and dehydration, substantially pure 3,4,3',4'-benzophenonetetracarboxylic dianhydride is recovered.

2. The process of claim 1 wherein the impure ortho-xylene mixture has the following composition (broad ranges):

| Compound | Volume Per Cent |
|---|---|
| ortho-Xylene | 88 to 98 |
| meta-Xylene | 0 to 3 |
| para-Xylene | 0 to 2 |
| Ethylbenzene | 0 to 1 |
| Components Boiling Above ortho-Xylene | 0 to 3 |

3. The process of claim 1 wherein the impure ortho-xylene mixture has the following composition (preferred ranges):

| Compound | Volume Per Cent |
|---|---|
| ortho-Xylene | 94 to 96 |
| meta-Xylene | 0 to 2 |
| para-Xylene | 0 to 1 |
| Ethylbenzene | 0 to 1 |
| Components Boiling Above ortho-Xylene | 0 to 2 |

4. The process of claim 1 wherein said condensation is carried out using from about 2.0 to about 20 mols of the impure ortho-xylene mixture per mol of acetaldehyde in contact with sulfuric acid at a temperature of about 5° to about 60° C.

5. The process of claim 1 wherein said condensation is carried out using from about 2.5 to about 5.0 mols of the impure ortho-xylene mixture per mol of acetaldehyde in contact with sulfuric acid at a temperature of about 10° to about 30° C.

6. The process of claim 1 wherein said oxidation is carried out using nitric acid having a concentration of about five to about 70 percent at a temperature of about 110° to about 350° C. for a period of about one minute to about 48 hours.

7. The process of claim 1 wherein said oxidation is carried out using nitric acid having a concentration of about 20 to about 40 percent at a temperature of about 150° to about 250° C. for a period of about 10 minutes to about two hours.

8. The process of claim 6 wherein at the end of the nitric acid reaction the reaction mixture is cooled to obtain a crystalline precipitate and the crystalline precipitate is heated at a temperature of about 110° to about 320° C. for about one-half hour to about 24 hours to obtain the substantially pure 3,4,3',4'-benzophenonetetracarboxylic dianhydride.

9. The process of claim 6 wherein at the end of the nitric acid reaction the reaction mixture is cooled to obtain a crystalline precipitate and the crystalline precipitate is heated at a temperature of about 150° to about 280° C. for about one to about 16 hours to obtain substantially pure 3,4,3',4'-benzophenonetetracarboxylic dianhydride.

* * * * *